(12) United States Patent
Radford et al.

(10) Patent No.: US 12,354,717 B2
(45) Date of Patent: Jul. 8, 2025

(54) PATIENT SAMPLE TRACKING SYSTEMS AND METHODS

(71) Applicant: Radeas, LLC, Wake Forest, NC (US)

(72) Inventors: Philip Radford, Wake Forest, NC (US); Matthew Wright, Wake Forest, NC (US)

(73) Assignee: Radeas, LLC, Wake Forest, NC (US)

( * ) Notice: Subject to any disclaimer, the term of this patent is extended or adjusted under 35 U.S.C. 154(b) by 530 days.

(21) Appl. No.: 17/528,176

(22) Filed: Nov. 16, 2021

(65) Prior Publication Data

US 2022/0157422 A1 May 19, 2022

Related U.S. Application Data

(60) Provisional application No. 63/114,357, filed on Nov. 16, 2020.

(51) Int. Cl.
*G16H 10/00* (2018.01)
*G06K 7/14* (2006.01)
*G16H 10/60* (2018.01)

(52) U.S. Cl.
CPC ............. *G16H 10/60* (2018.01); *G06K 7/143* (2013.01); *G06K 7/1447* (2013.01)

(58) Field of Classification Search
CPC ....... G16H 10/60; G06K 7/143; G06K 7/1447
See application file for complete search history.

(56) References Cited

U.S. PATENT DOCUMENTS

| | | | |
|---|---|---|---|
| 10,244,973 B2 * | 4/2019 | Holmes | B65D 81/18 |
| 10,832,806 B1 * | 11/2020 | Baek | G16H 20/13 |
| 11,275,914 B2 * | 3/2022 | Hagen | G06K 7/10811 |
| 2016/0015598 A1 * | 1/2016 | Provencher | G09F 3/10 |
| | | | 235/494 |
| 2016/0016165 A1 * | 1/2016 | Provencher | G09F 3/0297 |
| | | | 422/549 |
| 2018/0082043 A1 | 3/2018 | Witchey et al. | |
| 2018/0214058 A1 | 8/2018 | Holmes et al. | |
| 2018/0339433 A1 * | 11/2018 | Lin | B29C 45/263 |
| 2022/0020455 A1 * | 1/2022 | Cauley, III | B01L 3/502715 |

FOREIGN PATENT DOCUMENTS

EP 1986927 A2 11/2008
JP 2022015923 A * 1/2022 ............. G01N 15/05

* cited by examiner

*Primary Examiner* — Khai M Nguyen
(74) *Attorney, Agent, or Firm* — Michael Best & Friedrich LLP

(57) ABSTRACT

A system for collection and tracking of a sample for testing is provided, which includes a kit having a housing configured for storing a sample therein and a label for adhering to the housing upon contact. The label further includes images orientated both horizontally and vertically, each displaying the same readable context able to be scanned. The images are positioned such that the position of the label on the housing and the orientation of the reader scanning the images minimally affects the ability to read the images.

13 Claims, 6 Drawing Sheets

PATIENT SAMPLE TRACKING SYSTEMS AND METHODS

FIELD OF THE INVENTION

The present invention relates generally to systems and methods for tracking sample collection and analysis. Specifically, a sample may be linked to a mobile device for providing immediate access to sample analysis to the patient from whom the sample was collected.

BACKGROUND OF THE INVENTION

Traditionally, the process of collecting samples from patients, analyzing the samples and providing the analysis to the patient is a cumbersome, inefficient process that often results in errors. Service providers find themselves in a heavily regulated environment, due to the personal health information (PHI) involved, the serious of the PHI involved and the need to adequately store and process samples. Errors in sample labeling or misidentification of patients can frequently result in hardships and litigation, which drives up operating costs and erode trust and brand value.

There remains a need for systems and methods that permit efficient and secure tracking of samples and identification of the patient. Further, there remains a need to deliver sample analysis and results in a timely, efficient and secure manner. Disclosed herein are one or more systems and methods that advantageously address these issues.

SUMMARY OF THE INVENTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

According to at least one embodiment of the invention, a system for collection and tracking of a sample for testing is provided, including: a housing configured for storing a sample therein; a label having a first area for adhering to the housing upon contact and an opposing second area defining a first edge and an opposing second edge; a first image displaying readable content and positioned on the second area proximal to, and substantially parallel to, the first edge; a second image displaying the content and positioned on the second area substantially perpendicular to the first image, wherein the content, when read, is configured to convey information relating to the sample.

According to other embodiments of the invention, the system further includes a third image displaying the content and positioned on the second area.

According to other embodiments of the invention, wherein the third image is proximal to, and substantially parallel to, the second edge, such that if the label is adhered to the housing and overlaps itself, at least the content of one of the first image and the third image is readable.

According to other embodiments of the invention, wherein the second image is positioned between the first image and the third image.

According to other embodiments of the invention, wherein the third image is proximal to, and substantially parallel to, the second edge.

According to other embodiments of the invention, wherein the third image is sized substantially the same as the first image.

According to other embodiments of the invention, wherein the second image is sized substantially differently than the first image and the third image.

According to other embodiments of the invention, further including a fourth image displaying readable second content and positioned on the second area between the first image and the third image.

According to other embodiments of the invention, wherein the content and the second content are displayed differently but contain substantially similar information resulting in substantially similar functionality when read.

According to other embodiments of the invention, wherein the housing is substantially cylindrical.

According to other embodiments of the invention, wherein the images are orientated such that at least one of the images is readable irrespective of the orientation of a reader.

According to other embodiments of the invention, further comprising text positioned on the second area.

According to other embodiments of the invention, wherein the second area is a writable surface.

According to other embodiments of the invention, wherein the fourth image is a QR code and the first image, the second image and the third image are barcodes.

According to other embodiments of the invention, further including a reader for scanning the images and reading the content.

According to other embodiments of the invention, further including: instructions for using the system; a writing implement for writing on the label; a container for storing the housing, the label, the instructions and the writing implement, wherein the housing includes a cap for securing a sample swab and extracting solution therein, wherein the label is fastened to a removable backing.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

DETAILED DESCRIPTION OF THE INVENTION

Figure 1:
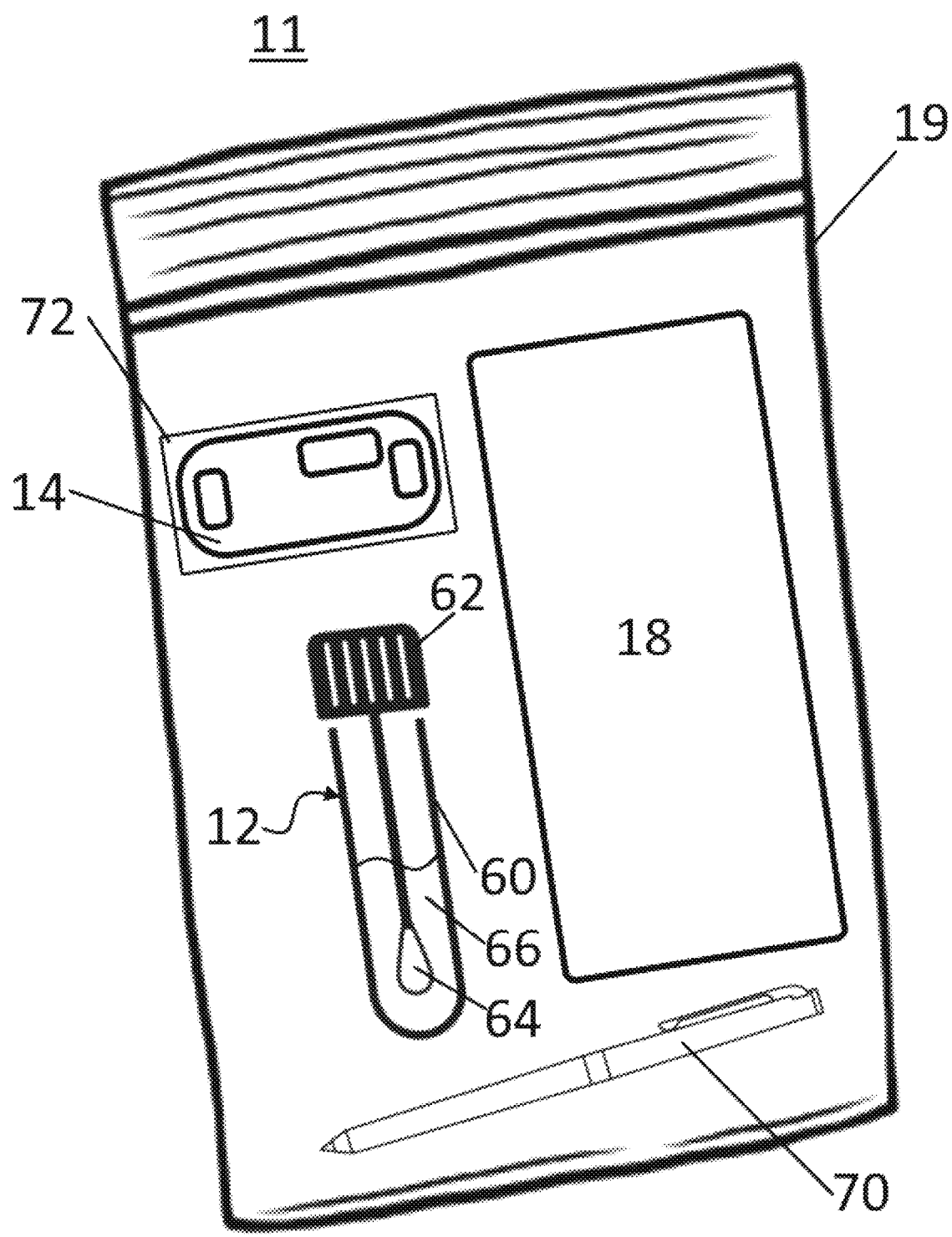
FIG. 1 is a perspective view of the container in which instructions, the label, the housing and the writing implement is stored according to at least one embodiment of the invention.

The following description and drawings are illustrative and are not to be construed as limiting. Numerous specific details are described to provide a thorough understanding of the disclosure. However, in certain instances, well-known or conventional details are not described in order to avoid obscuring the description.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

System Generally. As will be appreciated by one of ordinary skill in the art in view of this disclosure, the invention may be embodied as an apparatus (including, for example, a system, machine, device, computer program product, or any other apparatus), method (including, for example, a business process, computer-implemented process, or any other process), a system, a computer program product, and/or any combination of the foregoing. Accordingly, embodiments of the invention may take the form of an entirely software embodiment (including firmware, resident software, micro-code, etc.), an entirely hardware embodiment, or an embodiment combining software and hardware aspects that may generally be referred to herein as a system 10. The system 10 may include one or more collection housings 12, one or more labels 14, and/or one or more machine-readable images 16.

Physical Components. In some embodiments, and referring to FIG. 1, a physical kit 11 of the system 10 may include one or more sample collection housings 12, one or more sample labels 14 and/or one or more sample machine-readable images 16. The kit 11 may further include instructions 18 and/or a writing implement 70. In some embodiments, the kit 11 may include a container 19 for housing and transporting at least the components of the kit 11. The container may be a resealable bag, for example. One or more of the images 16 may be positioned on the housing 12, the label 14, the instructions 18, and/or some other component of the kit 11.

The sample housing 12 may be shaped and configured for receiving and storing the sample 3 and/or other materials 66. The housing 12 may include a body 60 and a cap or lid 62, which may be selectively fastened to the body 60 for securing the sample 3 and/or other materials 66 within the housing 12. In some embodiments, the kit 11 may include a housing 12 including materials 66 stored therein for mixing with a sample 3 when the sample 3 is received by the housing 12. For example, the materials 66 may include an extraction solution or reagent for mixing with the sample 3 and aiding in the analysis thereof. In some embodiments, the body 60 of the housing 12 may be substantially cylindrically shaped.

The housing 12 may further be configured for storing a swab 64 therein. The swab 64 may be coupled to the cap 62. The swap 64 may be used to collect a sample 3 and for placing the sample 3 into the housing. The swap 64 may include a cotton tip and stem and may be configured so that when the swap 64 is within the body 60 of the housing 12, the cotton tip containing the sample thereon may be immersed in the materials 66 when the housing is properly orientated.

The label 14 may be shaped and configured for selectively coupling with the housing 12. The label 14 may be adhered to a removable backing 72. In some embodiments, the label 14 is a rounded rectangle, though any number of shapes and configurations may be envisioned. The label 14 may include a printed side 54 for displaying information, such as one or more images 16, and an adhering side 56 for selectively coupling with the housing 12. The adhering side 56, which is initially adhered to the backing 72, may include an adhesive or other substance or feature disclosed by the prior art for permitting removal from the backing 72 and selective coupling with the housing 12 or another object.

Figure 2:
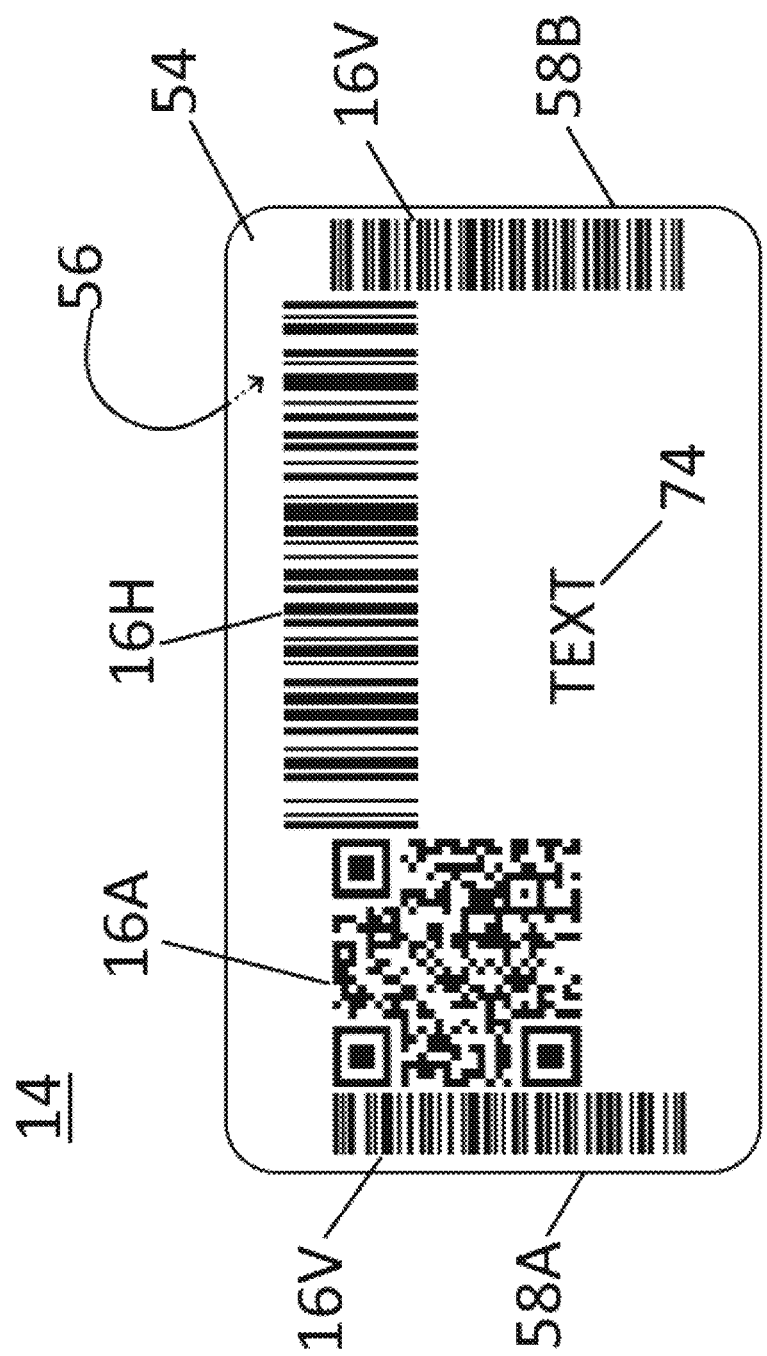
FIG. 2 is a top view of the label including images available for scanning according to at least one embodiment of the invention.

The sample image 16 may be any machine-readable feature, such as a barcode (e.g., QR barcode, other matrix barcode, or traditional barcode) or RFID. In one embodiment, one or more images 16 are positioned directly on the housing 12. In another embodiment, one or more images 16 are positioned directly on the label 14, which may be affixed to the housing 12. At least one embodiment of a label 14 including images 16 is depicted in FIG. 2, which includes two vertical images 16V, a horizontal image 16H and an agnostic image 16A. Each of the images 16H, 16V, 16A may include the same content, albeit in different formats according to the type of image being used. For example, 16A may be a QR code and 16H may be a barcode, but a reading of each image will perform the same function (namely, according to some embodiments, launching a website or application and displaying information tied to the particular label 14, and therefore sample 3, being read). In other embodiments, some images 16, when read, may including different content performing different functions.

In some embodiments, such as is depicted in FIG. 2 the label 14 (or housing 12 in other embodiments) may define two opposing sides 58A, 58B. Though the left and right sides are depicted as the two opposing sides 58A, 58B in FIG. 2, the top and bottom sides may be the two opposing sides 58A, 58B in other embodiments, and with non-rectangular shapes the two opposing sides may be differently defined. In embodiments where the label is irregularly shaped, or non-linear, "opposing sides" may be defined as merely being two opposite edges distally spaced from each other.

Two identical vertical images 16V may be positioned on the label, with one of the images 16V being placed proximal to one opposing side 58A and the other of the images 16V being placed proximal to the other opposing side 58B. Further, between the two vertical images 16V, a third, horizontal image 16H may be positioned on the label 14. In an alternative embodiment, two opposing sides 58 of a label 14 may each have proximally positioned identical horizontal images 16H, with a vertical image 16V being positioned therebetween. In each of the embodiments in this paragraph, the horizontal and vertical images 16H, 16V may be identical in content, even though they may be dissimilar in size or orientation, as depicted in FIG. 2.

By positioning two identical images 16 either horizontally or vertically proximal to opposing sides 58, and having a differently orientated image 16 therebetween, the present invention advantageously ensures that a reader of the label 14 will be able to successfully read at least one of the images 16, regardless of how the label 14 is affixed to the housing 12. For example, referring to FIG. ##, if the label 14 is wrapped around the body 60 of the housing 12, such that the label 14 overlaps itself and covers one of the vertical images 16V and part of the horizontal image 16H, the remaining vertical image 16V may still be readable. Numerous positionings of the label 14 about or onto the housing 12 may result in one or more of the images 16 being partially or fully obstructed from reading; however, the unique configuration envisioned herein, where there are two images of the same orientation proximally positioned to opposing sides 58, and having another image 16 with a differing orientation (substantially ninety or two-hundred and seventy degrees difference, or substantially perpendicular) positioned therebetween, ensures that at least one image 16 is always readable. This is particularly useful when a reader is being used that is orientation-dependent, in other words, the reader's functionality depends on aligning the reading element, such as a laser, with at least one of the images 16.

In an alternative embodiment, only two images 16 are positioned on the label 14 or housing 12 to maximize readability. In such an embodiment, the two images 16 each have a different orientation, one being substantially horizontal and the other being substantially vertical. According to one embodiment, referring to FIG. 2, for example, the vertical image 16V proximal to side 58A would be positioned the same, the second vertical image 16V would be removed, and the horizontal image 16H would be shifted to the right and proximal the side 58B. In this manner, having a vertical image 16V proximal one side 58A and having an image 16H orientated substantially perpendicular to the first and proximal an opposing side 58B maximizes the chance that a positioning of the label 14 on or about a housing 12 will result in at least one readable image 16. In each embodiment, the positioning of at least two images 16 having substantially perpendicular placements on the label 14 maximizes the chances that a reading of the label 14 will result in at least one image being read (regardless of the position or orientation of the device reading the label 14).

Instructions 18 may also be received by the patient 1 and/or provider 2, which may be printed or digital and may include information informing the patient 1 and/or provider on how to use the system 10, housing 12, label 14 and/or image 16 for tracking a collected sample 3 and/or any of the data associated therewith. The instructions 18 may further instruct the patient 1 and/or provider 2 on how to download and/or operate apps and/or software 110 for reading the image 16, communicating within the system 10 (including accessing the system portal 120, which may be a SaaS dashboard or website), and/or viewing or sharing the data.

System Architecture. The system 10 for tracking a sample 3 and communicating sample data between provider(s) 2, patient(s) 1 and/or third-party(ies) 6 may be implemented as a client/server architecture wherein communications may occur using computing device(s) 4, 5, 7 with a central hub (e.g., server) 100. The server 100 may be a physical server or a virtual server. In other embodiments, the server 100 may be located on a company premise or located in any other type of datacenter. The server 100 may also be configured as a plurality of physical servers and/or virtual servers. In some embodiments, a server may provide the virtual server and may be implemented as a separated operating system (OS) running on one or more physical (i.e., hardware implemented) servers. Any applicable virtual server may by be used for the server function. The server 100 may be implemented within a cloud computing data center environment or the like.

A computing device 4, 5, 7 may be a fixed device or a mobile device. A patient may use a patient computing device 4, a provider may use a provider computing device 5, and/or a third-party may use a third-party computing device 7. For example, a fixed device may be an interactive kiosk, a personal computer, or the like. A mobile device may be any computing device capable of being transported easily from a one location to another location without undue difficulty and one that is capable of functional connection with a remote server regardless of its location. For example, a mobile device may be a smart phone, a tablet, a personal digital assistant, a laptop, or the like. In general, a computing device 4, 5, 7 as used with the system 10 may be any computing device providing a user input, display, and connectivity to one or more servers over a personal area network (PAN), a local area network (LAN) and/or a wide area network (WAN). The PAN may include Bluetooth® or Universal Serial Bus (USB). The LAN may include any combination of wired Ethernet and/or Wi-Fi access points. The WAN may include the Internet and/or another wide area private network. The WAN may also include any combination of 2G, 3G, 4G, and 5G networks. In some embodiments the WAN may include Data Over Cable Service Interface Specification (DOCSIS) networks and/or fiber networks such as passive optical networks (PONs). Access to the one or more servers may also be provided via a virtual private network (VPN) within any of the previously described networks.

Figure 3:
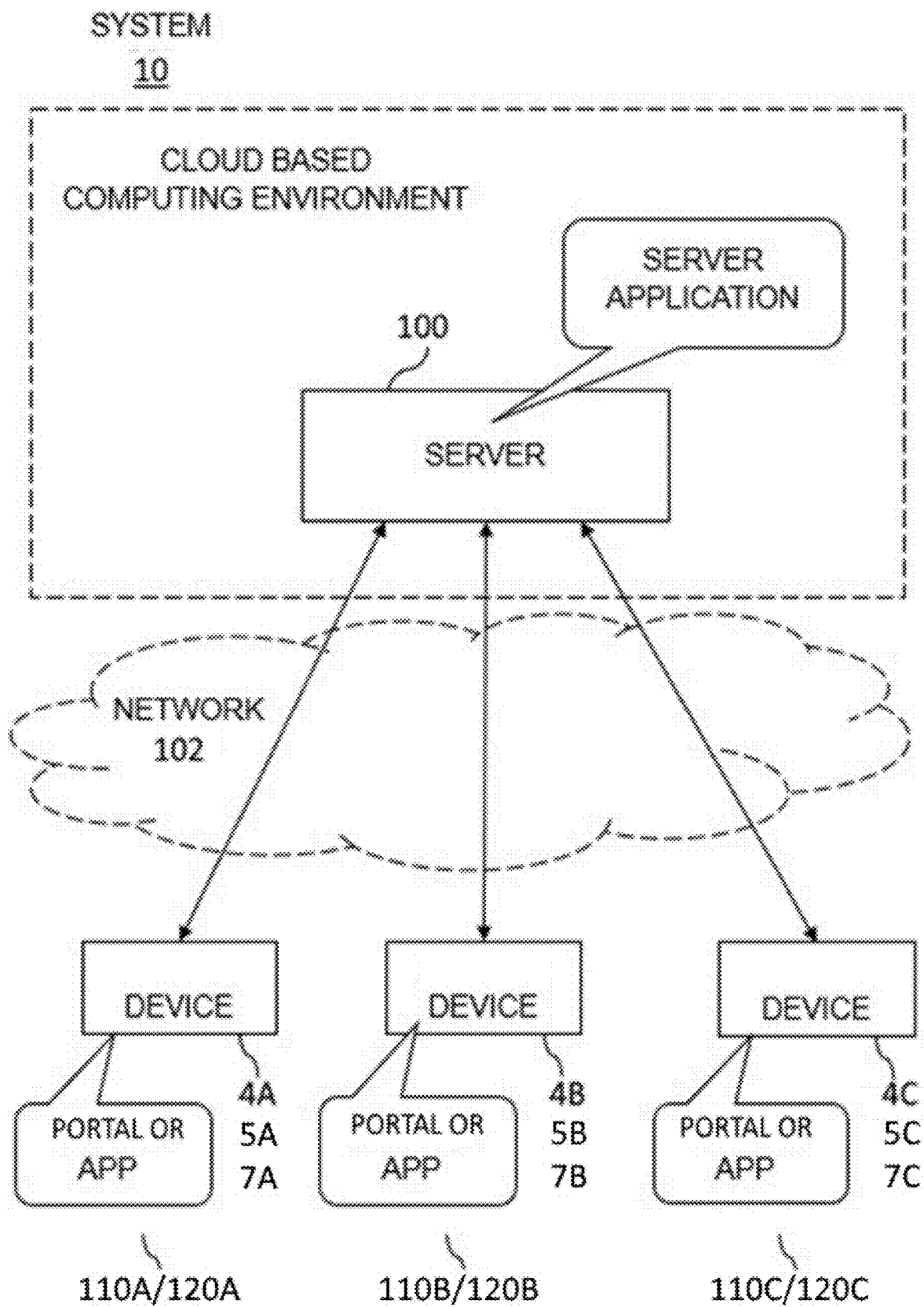
FIG. 3 is a schematic drawing of the system and communication architecture according to at least one embodiment of the invention.

System Communication. A system 10 for facilitating collection of a sample 3, analysis and exchange of sample data, patient data and provider data between patient(s) 1, provider(s) 2, and/or third-party(ies) 6 is disclosed herein. FIG. 3 depicts one embodiment of the system 10 in communication with a plurality of computing devices 4, 5, 7 each hosting a mobile application 110 or accessing a website 120 according to at least one embodiment of the system 10. Although FIG. 3 depicts various mobile devices 4, 5, 7 in communication with a single server 100 over a single network 102, a plurality of servers and/or networks may be used. The cloud based computing environment may include one or more virtual servers running server applications.

The system 10 may communicate with the patient computing device(s) 4, provider computing device(s) 5 and/or third-party computing device(s) 7 via an app or software 110, or through a software as a service (SaaS) dashboard or website 120. The system 10 may be combined with mobile technology, such that a patient 1, provider 2 and/or third-party 7 may enter the system 10 with a mobile device 4, 5, 7 by simply going to the dashboard or website 120 and/or opening an application or software 110.

The patient 1 and/or provider 2 may download the app or software 110 and/or directly log into the system portal 120 to register and log onto the system 10. In some embodiments, the patient 1 and/or provider 2 may register by creating a unique ID and/or password that identifies the patient 1 and/or provider 2 in the system 10. In some embodiments, the patient 1 and/or provider 2 may download and/or install the app or software 110 and scans the image 16. The scanning of the image 16 may be performed using a third-party software application or application native to the device 4, 5, 7, either independently or through the app or software 110 or portal 120 associated with the system 10. Upon scanning the image 16, the patient 1 and/or provider 2 may be provided all or a portion of the instructions 18.

Figure 4:
FIG. 4 is a view of a screenshot of an application for displaying sample analysis according to at least one embodiment of the invention.
Figure 5:
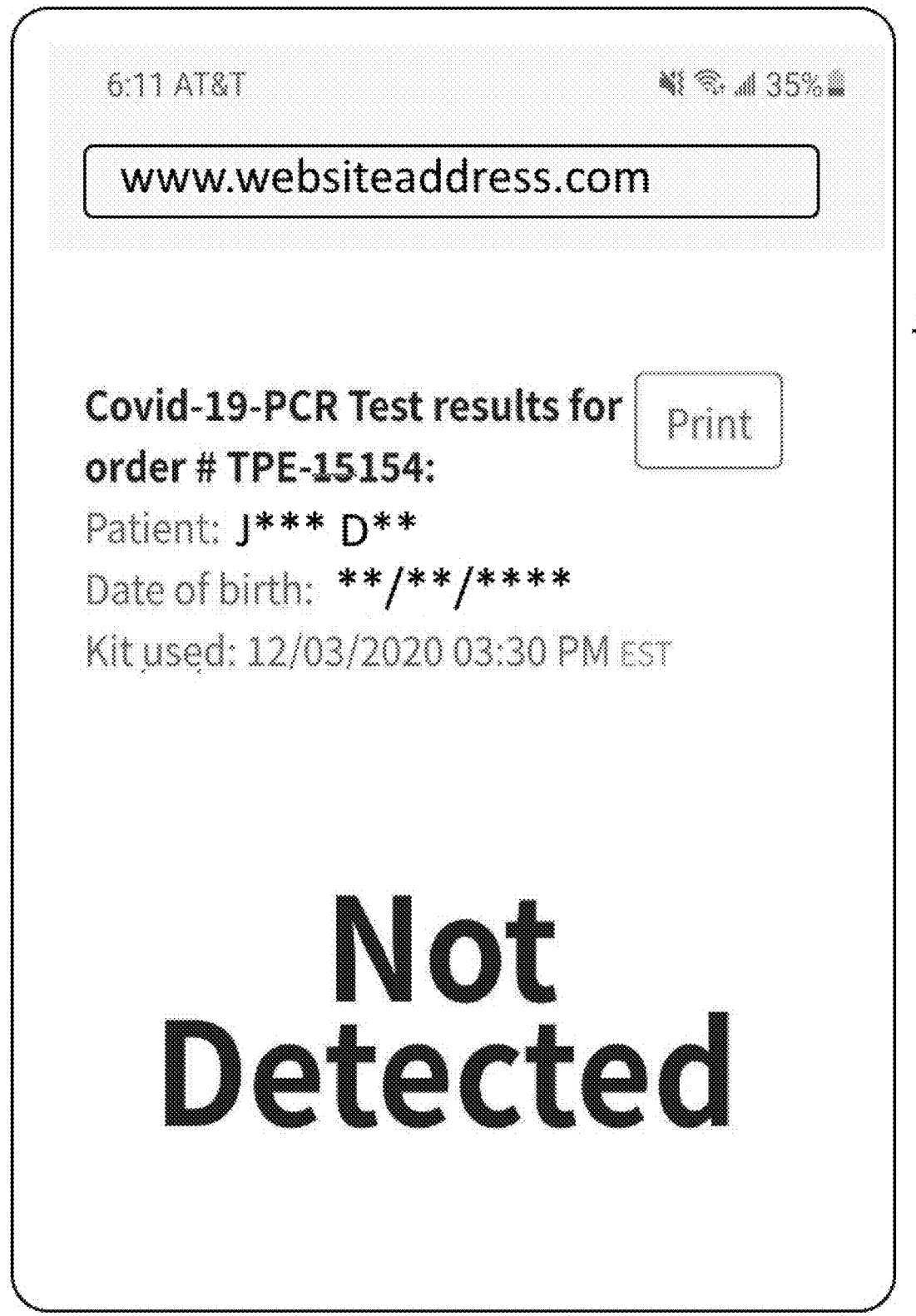
FIG. 5 is a view of a screenshot of a website for displaying anonymized sample analysis according to at least one embodiment of the invention.

The patient 1 may use a patient device 4 for reading the image 16. The reading of the image 16 may trigger the portal 120 through which the patient 1 may interact with the system 10. The portal 120 may be a Uniform Resource Locator (URL) for accessing the portal dashboard or website 120. In another embodiment, as depicted in FIG. 4, an application or software 110 may permit interaction with the system 10. FIG. 5 depicts a dashboard or website 120 being viewed by a third-party 6.

When a patient 1 and/or provider 2 uses their device 4, 5 to read the image 16, the system 10, through any of its components, may collect and store sample data, patient data and/or provider data. In one embodiment, when a patient device 4 reads an image 16, the system 10 may collect patient data such as patient device identification data, patient device location data, a timestamp, and/or patient bibliographic data. Patient data may include signatures, initials, and/or date of birth of the patient 1. Some or all of this patient data may be automatically collected by the system 10 without further action by the patient 1. The patient device identification data may include any one or more of the following: the operating system being used by the patient device 4; the particular model of the patient device 4; the communication network being used by the patient device 4; the MAC address, IMEI, MIN/MSIN, SIM, IMSI, IP address and/or MSISDN for the device 4; and other software or application data related to the device 4.

Further, upon reading the image 16, the system 10 may collect and store sample data, which may include image data and sample data. The system 10 may automatically collect the image data for associating the specific image 16 to the corresponding sample 3. The sample data be stored in the system 10 prior to the patient 1 receiving the sample image 16, such that the image 16, sample housing 12 and/or sample label 14 were associated with each other in the system 10 prior to the patient receiving the sample image 16. Further, the provider 2 or a third party 6 may have associated and stored certain sample data (e.g., what is to be collected, storage and transport instructions) or patient bibliographic data with the image 16 prior to the receipt or reading of the image 16 by the patient 1.

In other embodiments, the system 10, upon reading the image 16, may indicate to the patient 1, through the app or software 110 or portal 120, a request for some or all of the patient bibliographic data. The bibliographic data may include the name, mailing address, contact information, date of birth, personal health information and/or any other information associated with the patient 1. Contact information may include a preferred mode of communication, an emergency contact, a phone number, an email address or other relevant contact information. In some embodiments, the system may create a unique patient identification for associating all the bibliographic data and/or contact information therewith. The patient ID, upon the reading of an image 16 and/or upon the receipt of bibliographic data or contact info, may be associated with the image 16 and/or sample 3 in the system 10. A secondary patient ID may be received by the system 10 for confirming the identity of the patient 1. The secondary patient ID may include the patient's date of birth or email address or may include a unique access code or identification provided by the system 10 which may be used by the system 10 or with third parties 6 to anonymously permit patient 1 access.

After successfully securing the sample 3 and ensuring that the image 16 is affixed to the sample housing 12 (either through affixing the label 14 or having already been incorporated on the housing 12), the patient 1 may read the image 16 using the patient device 4. The provider 2 or a third party 6 may have stored certain of the sample data, patient data and/or provider data in the system 10 prior to the patient 1 receiving the housing 12 and image 16. In some embodiments, some or all of the data may be retrieved by the system 10 upon the reading of the image 16 and/or may be provided by the patient 1 through the app or software 110 or portal 120.

In some embodiments, after reading the image 16, the system 10 may create a unique patient portal 120U, unique patient ID and/or a unique patient access code corresponding to the patient 1 (and each may be stored in the system 10 as sample data and/or patient data). The patient 1 may be provided the unique portal 120U, ID and/or code through the portal 120U or app or software 110, or through utilization of the contact information. After securing the sample 3, the patient 1 may transport the sample 3 to the provider 2 or a third party 6 (who may then transport the sample 3 to the provider 2) for analyzation of the sample 3. The unique patient portal 120U, unique patient ID and/or a unique patient access code corresponding to the patient 1 may permit the patient 1 (and/or provider 2 or third party 6) to track the sample data 20 in real-time.

Sample data may include the sample location, sample testing procedures, sample analysis and/or post-analysis instructions. In some embodiments, the patient 1 may receive a notification including the patient access code via email or text (contact information), and the access code may be embedded with a hyperlink for launching the patient's unique URL 120U on the patient device 4. Upon launching the unique URL 120U, the access code and/or other patient data (e.g., the patient ID) may be auto-filled, thereby granting the patient 1 immediate access to the information provided through the unique URL 120U. A similar process may be initiated when the patient 1 reads the image 16, which may be provided in duplicate to the patient 1 upon initial receipt of the sample housing 12. In some embodiments, the system 10 may be configured to prevent certain information (e.g., personal health information) from being included in notifications.

In other embodiments, the method described in the preceding paragraph may require additional authentication by the patient 1 before information is displayed through the unique URL 120U. For example, the patient 1 may need to provide additional patient data, such as a date of birth, a fingerprint scan or some other data or form of two-factor authentication.

The system 1 may provide additional notifications to the patient 1. The notifications may be automatically pushed by the system 1 and/or pushed by the provider(s) 2 or third party(ies) 6. For example, the system 1 may push a notification after a certain time period, or a provider 2 may push a notification upon receipt of a sample 3 or upon completion of analysis of a sample 3. The notification may be received by the patient 1 through the app or software 110, the portal 120, and/or through utilization of the patient contact information.

Similar to the patient interactions with the system 10 described above, any provider 2 and/or third party 6 may interact with the system 10 to provide, receive and/or retrieve data and send or receive notifications. In some embodiments, patient data may be displayed to the patient 1, along with a readable image 16 thereon (see, e.g., FIG. 4). Though the patient 1 may choose to display personally identifiable information or health information to a third-party 6, the system 10 operator or provider 2 may not have such permissions. Therefore, in order to show proof of a health status, medical condition or some other patient data related to the sample from the patient 1 to a third-party 6, the system 10 may enable the third-party 6 to scan an image 16 displayed in the app 110 or on the website 120, on the same screen as the patient data 22 needed by the third-party 6, such that reading the image 16 being displayed takes the third-party 6 to their own app 110 or a website 120 on their device to reveal anonymized patient bibliographic data, while still confirming the patient data in question (see, e.g., FIG. 5).

In FIG. 5, the patient's name is anonymized, which may be in various different formats, yet the results of the sample analysis remain. Such a system 10 enables a third-party to ensure that the patient 1 did not alter or 'doctor' the results (e.g., removing "NOT" from a "NOT DETECTED" result) by allowing the third-party 6 to independently verify the result. Further, the patient 1 may alter or doctor the readable image 16. In such cases, as depicted in FIG. 5, certain information displayed may be cross-checked with the patient's display of information, such as the "Kit used" date (or sample collection date), the order number, or certain anonymized bibliographic information (just the initials and number of letters are displayed in FIG. 5, for example).

The system 10 may use patient data to perform contact tracing automatically and to further use the notifications to enhance initial contact tracing analysis. For example, if a sample 3 of a patient 1 indicates the presence of a virus, then the system 10 may access stored patient data (which may include mailing address of patient 1 and/or device location(s)) and compare to the patient data of other patients 1. Further, the system 10 may request historical device location data from one or more patients, send notifications requesting additional information and/or notifying patients of potential exposure.

Any of the sample data 20 may be compared to public databases to identify potential clinical trials, health care providers, other vendors or resources, and/or private databases to match these sources to the sample data and provide such sources to the patient 1, provider 2 and/or third party 6. Such comparisons may be performed with the permission of the patient 1 and/or the sample data may be anonymized. Any of the data may be shared by the system 10 with one or more third parties 6; such data however, may be anonymized to remove personal identification of the patient 1.

Various methods of using the system 10 may be envisioned. A method for tracking the sample and data may include: storing the sample in the housing; adhering the label to the housing; the reader scanning the label for reading the content of the images; testing the sample to create sample data; logging sample data into the system and tying the sample data to the content of the images; and presenting the sample data. Additional steps may include retrieving the sample data by reading the image. One or more provider, personal or third-party devices may be linked to the image and therefore sample data prior to testing and therefore enable a push notification to one or more of these devices.

Figure 6:
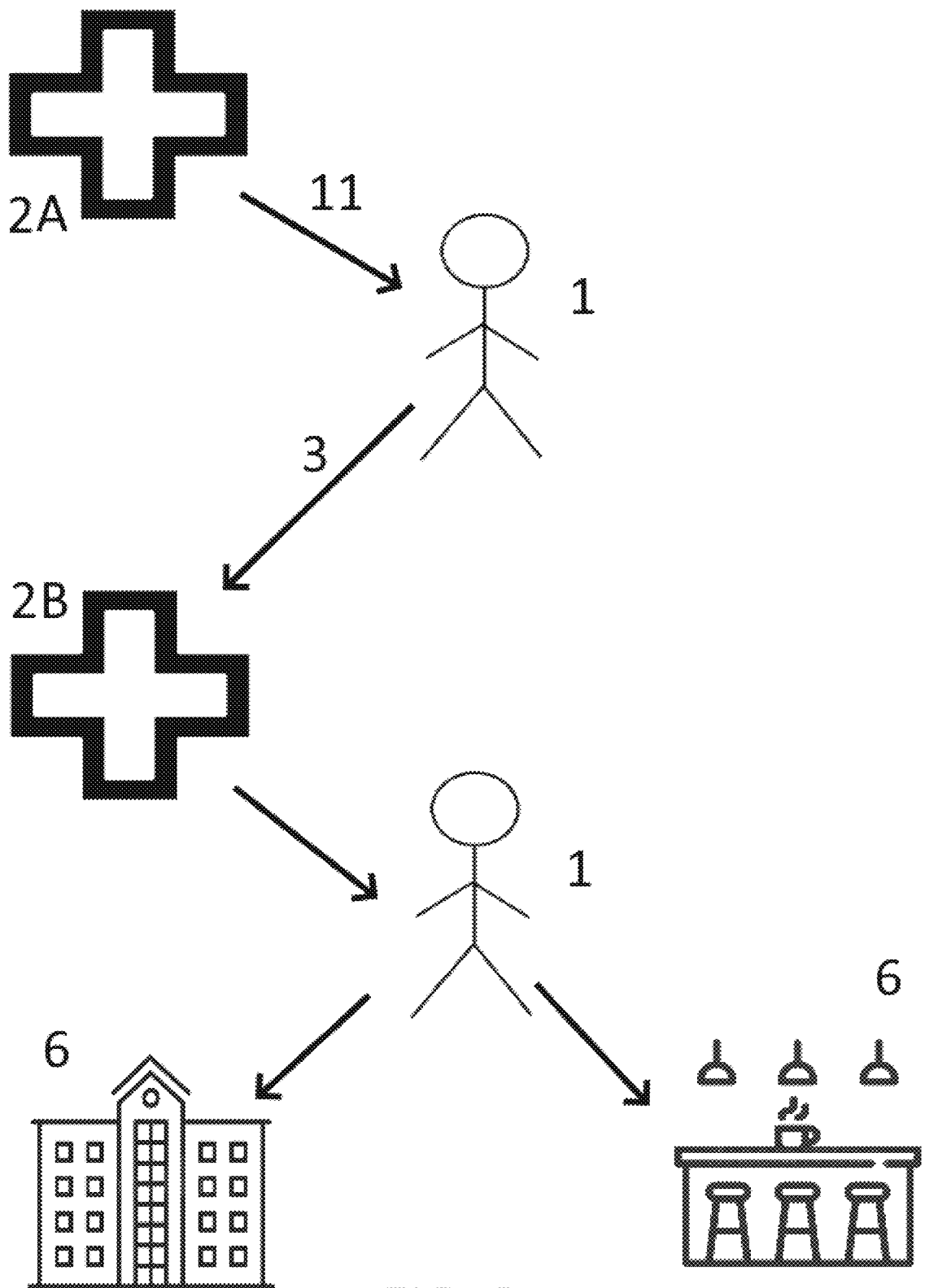
FIG. 6 is a schematic tracking the sample and analysis according to at least one embodiment of the invention.

In the method depicted in FIG. 6, a provider 2A provides a kit 11 to patient 1, who provides a sample 2 for analysis by provider 2B. The analysis of provider 2B is then accessed by patient 1, who shares specific analysis with one or more third-parties 6, like an employer or a restaurant.

Particular embodiments and features have been described with reference to the drawings. It is to be understood that these descriptions are not limited to any single embodiment or any particular set of features, and that similar embodiments and features may arise or modifications and additions may be made without departing from the scope of these descriptions and the spirit of the appended claims.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium (including, but not limited to, non-transitory computer readable storage media). A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable. RF, etc., or any suitable combination of the foregoing.

Computer program code for carrying out operations for aspects of the present invention may be written in any combination of one or more programming languages, including object oriented and/or procedural programming languages. Programming languages may include, but are not limited to: Ruby. JavaScript. Java. Python. Ruby, PHP. C, C++, C#, Objective-C. Go, Scala, Swift. Kotlin, OCaml, or the like. The program code may execute entirely on the user's computer, partly on the user's computer, as a stand-alone software package, partly on the user's computer, and partly on a remote computer or entirely on the remote computer or server.

Aspects of the present invention are described in the instant specification with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. Thus, for example, reference to "a user" can include a plurality of such users, and so forth. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The invention claimed is:

1. A system for collection and tracking of a sample for testing, comprising:
    a housing configured for storing a sample therein;
    a label having a first area for adhering to the housing upon contact and an opposing second area defining a first edge and an opposing second edge;

a first image displaying readable first content and positioned on the second area proximal to, and substantially parallel to, the first edge;
a second image displaying the readable first content and positioned on the second area substantially perpendicular to the first image,
a third image displaying the readable first content and positioned on the second area, wherein the third image is proximal to, and substantially parallel to, the second edge, and wherein the third image is sized substantially the same as the first image;
wherein the second image is positioned between the first image and the third image, and wherein the second image is sized substantially differently than the first image and the third image; and
a fourth image displaying readable second content and positioned on the second area between the first image and the third image,
wherein the readable first content, when read, is configured to convey information relating to the sample.

2. The system of claim 1, wherein the third image is proximal to, and substantially parallel to, the second edge, such that if the label is adhered to the housing and overlaps itself, at least the content of one of the first image and the third image is readable.

3. The system of claim 2, wherein the housing is substantially cylindrical.

4. The system of claim 3, wherein the images are orientated such that at least one of the images is readable irrespective of the orientation of a reader.

5. The system of claim 2, further comprising text positioned on the second area.

6. The system of claim 5, wherein the second area is a writable surface.

7. The system of claim 1, wherein the readable first content and the readable second content are displayed differently but contain substantially similar information resulting in substantially similar functionality when read.

8. The system of claim 1, wherein the fourth image is a QR code and the first image, the second image and the third image are barcodes.

9. The system of claim 1, further comprising:
wherein at least the readable first content of one of the first image and the third image is readable, if the label is adhered to the housing and overlaps itself,
wherein the housing is substantially cylindrical,
text positioned on the second area,
wherein the second area is a writable surface.

10. The system of claim 9, wherein the readable first content and the readable second content are displayed differently but contain substantially similar information resulting in substantially similar functionality when read.

11. The system of claim 9, wherein the images are orientated such that at least one of the images is readable irrespective of the orientation of a reader.

12. The system of claim 9, further comprising a reader for scanning the images and reading the content.

13. The system of claim 9, further comprising:
instructions for using the system;
a writing implement for writing on the label;
a container for storing the housing, the label, the instructions and the writing implement,
wherein the housing includes a cap for securing a sample swab and extracting solution therein,
wherein the label is adhered to a removable backing.

* * * * *